(12) United States Patent
Hanselka et al.

(10) Patent No.: US 7,694,575 B2
(45) Date of Patent: Apr. 13, 2010

(54) METHOD AND DRIVE FOR INFLUENCING THE MECHANICAL LOAD-BEARING CAPABILITY AND/OR LOADING OF A TECHNICAL STRUCTURE

(75) Inventors: Holger Hanselka, Darmstadt (DE); Tobias Melz, Darmstadt (DE)

(73) Assignee: Fraunhofer-Gesellschaft zur Forderung der angewandten Forschung e.V. (DE)

( * ) Notice: Subject to any disclaimer, the term of this patent is extended or adjusted under 35 U.S.C. 154(b) by 0 days.

(21) Appl. No.: 11/914,827

(22) PCT Filed: May 18, 2006

(86) PCT No.: PCT/EP2006/004766
§ 371 (c)(1),
(2), (4) Date: Jul. 2, 2008

(87) PCT Pub. No.: WO2006/122821
PCT Pub. Date: Nov. 23, 2006

(65) Prior Publication Data
US 2008/0264142 A1    Oct. 30, 2008

(30) Foreign Application Priority Data
May 19, 2005 (DE) .................. 10 2005 023 079
Sep. 13, 2005 (DE) .................. 10 2005 043 430

(51) Int. Cl.
*G01B 5/30* (2006.01)
(52) U.S. Cl. ...................................... 73/760
(58) Field of Classification Search ............. 73/76–860
See application file for complete search history.

(56) References Cited

U.S. PATENT DOCUMENTS

| 4,622,980 A | * | 11/1986 | Kunig ........................ 600/517 |
| 5,479,343 A | * | 12/1995 | Matoba et al. .............. 700/106 |
| 6,679,121 B2 | * | 1/2004 | Sonnichsen et al. .......... 73/660 |
| 6,816,757 B1 | * | 11/2004 | De La Ree et al. .......... 700/286 |
| 7,236,896 B2 | * | 6/2007 | Farkas et al. ................ 702/60 |

OTHER PUBLICATIONS

"Actively Combating Vibrations", Pressemeldung Fraunhofer-Institut LBF, Apr. 8, 2005, 2 pgs.
Mayer, D., Herold, S., Atzrodt, H., Proceedings of the Second European Workshop "Structural Health Monitoring 2004", University of Sheffield, Dept. of Mechanical Engineering, DEStech Publications, Inc., Jul. 709, 2004, pp. 1099-1105.

* cited by examiner

*Primary Examiner*—Max Noori
(74) *Attorney, Agent, or Firm*—Antonelli, Terry, Stout & Kraus, LLP.

(57) ABSTRACT

A method and a device are described for influencing the mechanical load-bearing capability and/or loading of a technical structure. The method of the comprises: detecting at least one loading-correlated characteristic of the structure; determining a loading state of the structure on the basis of the at least one detected characteristic; assessing the loading state of the structure; and generating at least one signal on the basis of the assessment of the loading state and on the basis of at least one target function, which is designed at least to optimize the lifetime of the structure, which signal is sent to at least one actuator, which is integrated within the structure or is applied to the structure, to activate said actuator for influencing the loading state.

14 Claims, 3 Drawing Sheets

METHOD AND DRIVE FOR INFLUENCING THE MECHANICAL LOAD-BEARING CAPABILITY AND/OR LOADING OF A TECHNICAL STRUCTURE

BACKGROUND OF THE INVENTION

Modern mechanical structures, for example supporting structures or units performing similar functions, must in most cases meet at least two contradictory design criteria, namely having as lightweight a design as possible, on the one hand, and having as high a load-bearing capability as possible in terms of dynamic and stationary load influences, on the other. Conventional, that is purely passively designed structures can only partially meet these requirements through suitable choice of material and suitable structural design. Therefore limits are imposed on the choice of material with regard to material and the definable structural design is subject to static and dynamic load-bearing capability limits, the exceeding of which may lead to irreversible structural damage which considerably reduces the total service life of the mechanical structure. In order to alleviate the indicated loading problem, mechanical structures or structures built by machine are deliberately designed so that they are oversized so that they are able, without damage, to withstand temporary, in the sense of short-term, load or loading peaks. However, this measure is taken to the detriment of both the weight of the structure and also the costs.

SUMMARY OF THE INVENTION

The invention is a device and a method for influencing the mechanical load-bearing capability and/or loading of a technical structure in order to either to design existing structures lighter with constant load-bearing capability, or to improve or increase the load-bearing capability of structures under a constant mass or weight. A further objective is to optimize the technical structure in terms of its mechanical design, for instance the production of a lighter structure with suitable lifetimes, such as a classically designed structure.

The invention influences the mechanical load-bearing capability of technical or mechanical structures or structural systems based upon the fundamental principle of adaptronics whereby, in a first step, a current loading state of the structure is detected by detecting sensorially at least one loading-correlated characteristic of the structure, preferably a mechanical characteristic, which varies under the static and/or dynamic loading influence on the structure. The loading state of the structure is determined on the basis of the at least one detected characteristic. In this case a database or knowledge store is accessed in which are stored loading states of the structure having at least one characteristic and that have preferably been previously obtained by means of calibrated reference measurements and are characterised by at least one characteristic detectable by measurement. The use of expert knowledge is also conceivable. The current loading state of the structure may be concluded in this manner by assignment of the characteristic detected by measurement.

In a further step it is necessary to evaluate the detected loading state of the structure according to the operating strength methods and processes, particularly in relation to a loading state that is regarded as critical and which the structure would assume under a maximum tolerable load. That is the exceeding of this loading state regarded as critical results in irreversible structural damage. In this context a degree or dimension is preferably determined which describes the so-called residual load-bearing capability of the structure which, when reached or exceeded, results in local or global irreversible damage to the structure.

On the basis of the assessed loading state, and when at least one target function is specified that covers at least conditions or criteria which are designed to maximise the lifetime of the structure, at least one signal is generated which is sent to at least one actuator integrated within the structure or applied to the structure, thereby influencing the loading state of the structure. The loading state is influenced by suitable activation of an actuator preferably integrated within the structure subject to an extension of the lifetime of the structure, where the action imposed by the actuator on the structure is able to develop load relieving, but also loading effects, depending on the case. For example, if improvement of a structure in terms of its stability and associated properties protecting against an external load application is desired, a suitably chosen actuator is able to strengthen or stiffen the specific structural region concerned. On the other hand, the increase in lifetime of the structure could be aided by specifically destabilizing certain regions of the structure or transferring them to a certain state in order to prevent crack formations or brittle fracture phenomena, for example, due to high frequency alternating loads acting externally on the structure.

In a particularly preferred method of the invention, the loading state is influenced by suitable activation of the actuator connected to the structure, that is integrated in the structure or applied to the structure, by way of an active control, i.e. the action directed by the actuator onto the structure is sensorially detected in real time conditions and assessed by a target function increasing the lifetime of the structure so that eventually the activation of the actuator is specifically controlled.

Depending on the material and the structural design of the structure to be taken into consideration, a plurality of actuators are preferably integrated in the structure or applied to the structure, preferably in regions of the structure which experience a particularly high load due to an external load influence, that is an extremely high material loads and associated fatigue phenomena. When a plurality of actuators associated with the structure are used, it is necessary to assess the loading state of the structure as a whole for controlled activation of all the individual actuators, and to take into consideration the mutual influence of all the actuators on the entire structure.

As an alternative to the actively controlled activation of an actuator connected to the structure, described above, the so-called semi-active influence also provides the possibility of influencing the mechanical load-bearing capability of a technical structure. In this case use is made of actuators whose actuator behavior is tailored to a specific actuator task. Unlike active control, where the actuator is operated by a suitable energy supply and control signals, a semi-actively operated actuator is operated without an external energy supply. Here the actuator does not act to actively introduce mechanical loads, but instead is an energy converter which converts the mechanical energy acting in the structure, which results from its loading, to preferably electrical energy, so that this electrical energy can now be processed in a connected electrical circuit. For example, an oscillatory circuit may be constructed or an energy recovery system established in this manner.

Typically such actuator systems have converter materials which are capable of converting energy between different forms of energy. Preferred representatives of such converter materials are piezoelectric materials such as piezoelectric ceramics, lead-free piezoelectric ceramics, shape memory alloys (SMA materials), as well as electrorheological fluids or electroactive polymers. For example, a method is known for influencing the material stiffness and damping behavior of such converter materials by means of an external energy supply. Depending on the converter material, the external energy supply may be an electrical, thermal or magnetic nature. Conversely deformations in such converter materials result in the generation of electrical energy, for example, which can be converted sensorially or semi-actively in the manner described above.

The invention is therefore based on the fundamental principles of adaptronics and combines them with the aspect of the operating strength of technical structures, where mechanical loading states of technical structures are detected and assessed and an actuator actively or semi-actively influences the loading state of the structure concerned for the purpose of increasing the lifetime of the structure. Obviously optimization of the technical structure can be achieved by suitable means in terms of its mechanical design, for example, the achievement of a lighter structure with suitable lifetimes, such as a classically designed structure.

The degree of utilization or the lifetime consumption of the technical structure can be assessed in this manner on the basis of current and accumulated loading characteristics detected by suitable sensors, and active lifetime-favorable influencing of the load-conditioned energy flows that exist within the technical structure can be achieved by means of one or a multiplicity of actuators connected to and/or integrated in the structure. The at least one actuator connected to and/or integrated in the structure is activated on the basis of a target lifetime-increasing function by the actuators installed, through which, when a plurality of actuators are used that are installed on and/or in the structure in a distributed manner, the load application to regions of the structure consumed over a longer lifetime, acting statically or dynamically on the structure, is reduced, for example, by active control of certain actuators, for example by energy reflection, whereas the load application to regions of the structure consumed over a shorter lifetime is stopped by active control of the energy transmission. Through a suitable choice and activation of the mechanical impedances that can be assigned to the actuators, regions of the structure that are subject to greater weakening or damage can be spared, and regions of the structure that are subject to less use can be loaded more heavily. The inventive concept of the actively controlled load redistribution within a technical structure therefore comes a decisive step closer to the objective of increasing a system lifetime or the objective of intelligent light construction, despite constant or even improved safety factors in terms of system reliability and operational strength. Prior art oversizing of structural components for the purpose of avoiding material overloads that may occur, if applicable, in the case of short-term and rare load elevations, can be avoided by means of the inventive method. Instead the inventive active structural influencing allows controlled monitoring of preferably all load-dependent energy flows passing through the structure so that a reaction is possible to variations in the acting operating loads or the loading states caused thereby inside the structure so that the load is resisted and lifetime is ultimately extended.

For implementing the method described above for influencing the mechanical load-bearing capability of a technical structure, a device according to the invention which is designed for this purpose provides at least one sensor which is integrated to the structure or is applied to the structure and generates a loading-correlated sensor signal which preferably varies on the basis of a structural deformation which the structure experiences under the influence of static and/or dynamic load. Sensors of converter materials or having converter materials, which generate an electrical signal indicating the current expansion state of the sensor, are preferably suitable for this purpose. The sensor signal obtained by means of the at least one sensor is sent to an evaluation unit which assigns a characteristic corresponding to the sensor signal, preferably a mechanical characteristic. Further, a database, for example in the form of a storage unit of prior art, in which are stored previously known loading states of the technical structure, preferably detected by reference measurements and/or by numerical and/or analytical measurements, and from which the evaluation unit selects an already assessed loading state as a function of the determined characteristic. It is also appropriate to use existing expert knowledge as an alternative or supplement to this in order to assess a loading state characterised by a detected characteristic. Finally an activating unit is provided which activates at least one actuator which is integrated in or applied to the structure in such a manner that the structure is loaded or load relieved at least in one local region as a function of the currently assessed loading state.

In a particularly preferred embodiment, the at least one sensor and the at least one actuator are designed as a single structural unit and have a converter material, as explained above, or are produced entirely from it, which material enables mechanical deformation energy to be converted to electrical energy and vice versa. The sensor and actuator are preferably integrated in conformity with the structure in high load bearing and highly loaded regions of the structure for direct detection of mechanical loads and the influencing of these loads.

In order to provide a device that operates as self-sufficiently and autonomously as possible, a preferred embodiment provides for the additional integration of the evaluation unit and of the database or storage unit having a data connection with the evaluation unit, in addition to the sensors and actuators within the structure. The above-mentioned components can be constructed in miniature form using intrinsically known microelectronic structural elements and applied to the technical structure in a manner that does not weaken the mechanical load-bearing capability of the structure.

It is also possible to provide the evaluation unit and the database separately from the technical structure and to carry out the required exchange of signals between the at least one sensor and actuator, each of which are connected to the structure, by means of a telemetry unit which is provided on the one hand with the structure and on the other in the location of the evaluation unit. In the case of static technical structures it is also possible to accomplish the data exchange on a wire-bound basis.

As an alternative to the integration or application of at least one sensor in or on the structure, it is also conceivable to detect the structural deformation caused by the external loading effect in the structure by means of a sensor system provided separately from the structure, for example a camera unit. However, it is not absolutely necessary to integrate the at least one actuator for influencing the loading state of the technical structure inside the structure, preferably in conformity with the structure, or to apply it to the structure in a suitably selected surface region.

BRIEF DESCRIPTION OF THE DRAWINGS

The invention is described below by way of example without limiting the general inventive concept with reference to exemplary embodiments with reference to the drawings, in which.

DETAILED DESCRIPTION OF THE INVENTION

Figure 1A:
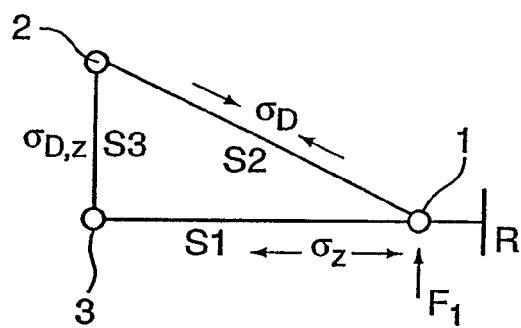
FIGS. 1a to d show a schematized representation for motivating the inventive method, FIGS. 2a, b show a schematized representation of the inventive principle on a bending wave.
Figure 1B:
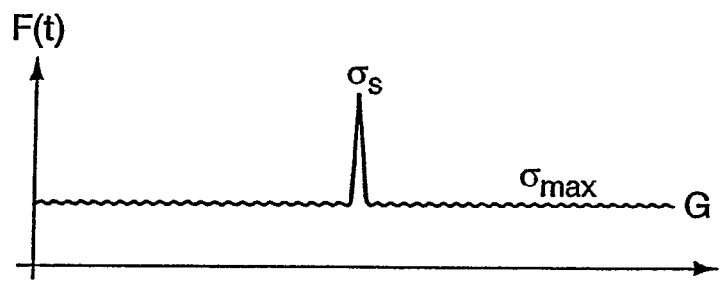

FIG. 1a represents, in highly form, the suspension points 1, 2, 3 of a triangular swinging arm of a motor vehicle, on whose suspension point 1 wheel R of the motor vehicle is mounted and whose suspension points 2 and 3 are arranged on the body side. Suitable tensile or compressive stresses S1, S2 and S3 $\sigma_D$ are shown with $\sigma_Z$, acting load-dependently along connecting struts S1, S2, S3. For the structural design of the triangular swinging arm consideration must be given to the vehicle weight, road reaction forces and short-term loads due to driving maneuvers, which must necessarily be used for dimensioning the structure. In this case consideration must also be given, in particular, to rarely occurring special loads $\sigma_S$ in an evaluated form (see the force-time graph F(t)/t graph according to FIG. 1b), which also have to be safely absorbed by the triangular swinging arm. Such special loads ultimately result in complete oversizing of the structure to be considered, for most of the time, in the form of the triangular swinging arm represented. Normally it would be sufficient, if one were to dispense with the influence of special loads, to design the structure according to a normally occurring maximum load $\sigma_{max}$, as represented in the force-time graph in FIG. 1b. However, since this is a safety component in the case of the triangular swinging arm, suitable special loads must be considered for such components or structures, which ultimately results in the oversizing of the structural design mentioned above.

It is therefore assumed, for example, that the motor vehicle is driven over a hole which exerts a vertically upwards directed force $F_1$ via wheel R to bearing 1. Such passing over a hole therefore results in a high compressive stress CD along connecting strut S2, whereas the other two struts S1 and S2 remain almost stress-free.

Figure 1C:
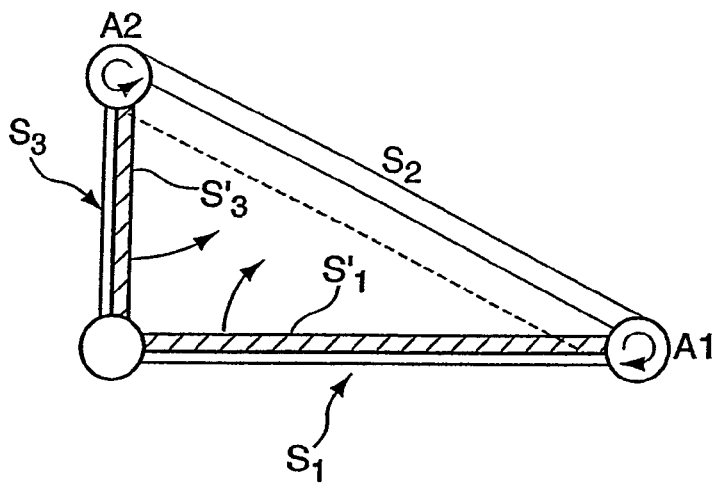

FIG. 1c shows a schematized exemplary embodiment of a triangular swinging arm whose connecting struts S1 and S3 are each designed so that they are split along their longitudinal extension, half of each of connecting struts S1', S3' being mounted so that they can be rotated or pivoted through actuator elements A1 and A2 and capable of adopting a pivoting condition running parallel to it for strengthening connecting strut S2. The mechanical load-bearing capability of connecting strut S2 can be temporarily strengthened by suitable activation of actuators A1 and A2 by applying connecting strut halves S1' and S3' along connecting strut S2. in order to resist the short-term special load $\sigma_S$ without damage.

Actuator elements A1 and A2 are preferably designed as energy converter systems capable of converting mechanical energy to electrical energy or, vice versa, to carry out electromechanical work by electrical activation. It is also conceivable to extract mechanical energy from the structure through suitable energy conversion and to dissipate it, for example by conversion to thermal energy in a connected electrical circuit. A further variant for operating an actuator would be the recovery of electrical energy by suitable conversion, whereby energy is withdrawn from the system.

Figure 1D:
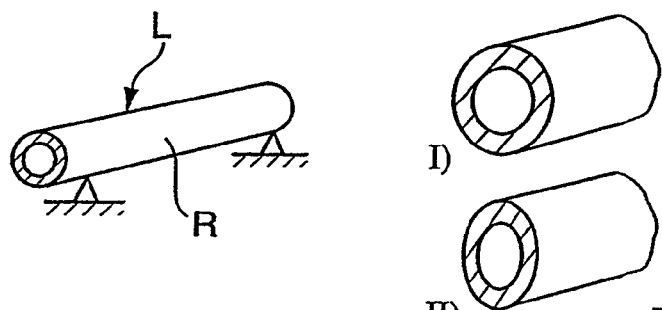

It is also conceivable for the actuator to effect a variation in cross-section of the technical structure for the purpose of improving the surface inertia properties and hence load-bearing capability. Thus a flexurally loaded structure, for example, in the form of a tube R, according to FIG. 1d, can be varied by varying the cross-section from a circular (I) to an elliptical (II) cross-section, either for the purpose of increasing the surface moment of inertia, in that the largest semi-axis of the elliptical cross-section is orientated in the direction of the acting load L, or for the purpose of increasing the flexibility of the structure, in that the largest semi-axis of the elliptical cross-section lies transversely to the acting load L. This can be achieved, for example, by monitoring the internal pressure of the structure. If an electrorheological or magnetorheological fluid is used for this purpose, actively controlled damping may also be introduced.

Figure 2A:
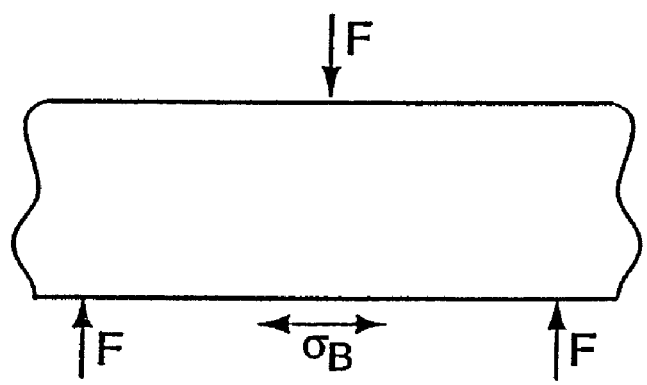
Figure 2B:
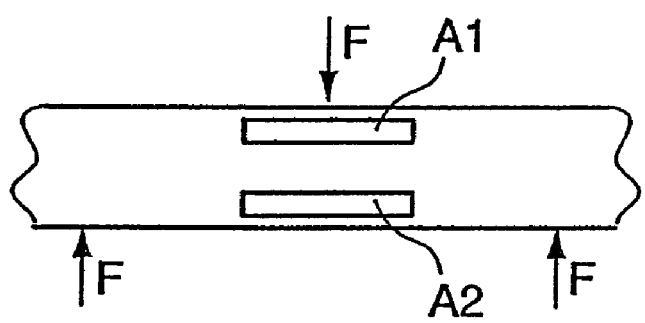

FIG. 2 shows, in a highly schematized fashion, a bending wave such as that used, for example, in printing machines or for railway wheels as a rotation axis. In the load case shown in FIG. 2b, forces F shown act on the load inflection regions indicated, which ultimately result in a deflection of bending wave and induce a tensile stress $\sigma_B$ within bending wave. If provision is made for two actuators A1 and A2 within bending wave, according to the invention, for example in the nature of piezo-actuators, additional force moments can be introduced into bending wave by activation of the actuators, which can compensate for the deflection of bending wave caused by the action of external forces or loads, so that no tensile stresses $\sigma_B$ loading bending wave occur. The activatable actuators A1 and A2 are therefore able to divert the load acting externally on bending wave into less critical regions, so that it is possible in this case to refer to an actuator controlled load diversion. Such an actuator arrangement is preferably suitable for reducing short-term load surges and eventually helps to avoid a conventional structurally required oversizing of the bending wave.

Figure 3:
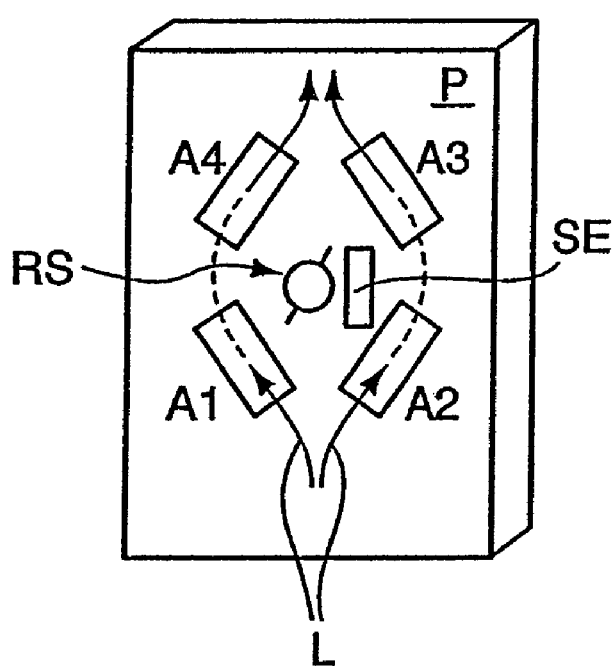
FIG. 3 shows a schematized representation of a plate-shaped component with a weakened structure region, FIGS. 4a, b shows a schematized representation of an integrated component, and FIGS. 5a, b shows a schematized representation of the inventive method on a plate placed on two fixed bearings.

FIG. 3 shows a further example of specific, controlled load deflection L within a plate-shaped structure P to avoid overloading of a structural region RS subject to cracking. As expected, structure P will fatigue under certain loads in the region of this weak point RS without additional measures, and will begin to crack. To avoid this, a sensor SE is provided for detecting local deformations within structure P in region RS, and four surface actuators A1 to A4 are provided for active load deflection, which actuators are able to introduce an external load action L into structure P due to suitable stiffening around the structural weak point RS.

Figure 4A:
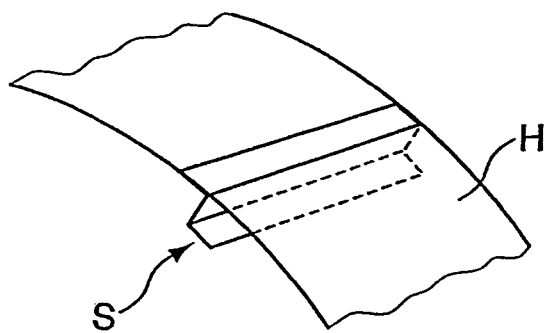

A further application example is shown in FIGS. 4a and b, in which it is necessary to stiffen superficially a large area skin panel H, as used, for example, in the outer wall paneling of aircraft. For this purpose so-called stringer elements S are used which create a physical connection of skin panel H to a substructure, not shown in detail, along their entire extension. The invention now enables the stringer element to be designed with a reduced size, in the form of two stringer element deflection points SA1 and SA2, which are connected to an actuator A for short-term mutual stiffening. Actuator A is only activated in cases where an overloading state is detected. It is assumed that actuator A also has sensory functional characteristics.

Figure 4B:
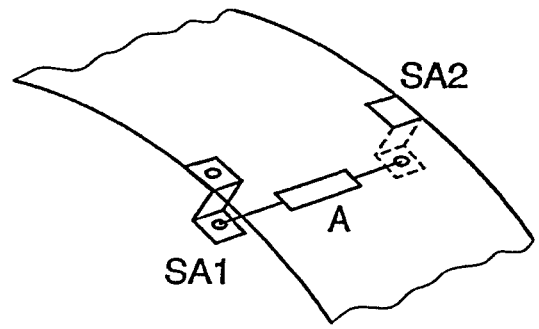
Figure 5A:
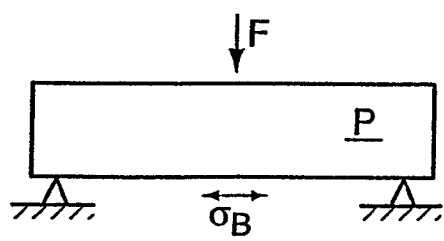
Figure 5B:
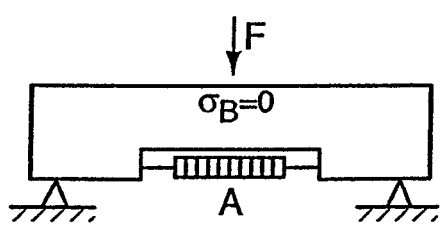

FIG. 5 shows the case of a loaded plate which is supported at two support points. As in the case shown in FIG. 2, a bending stress $\sigma_B$ is also induced by a force F acting on plate P, which stress is compensated according to the invention by using an actuator A according to the arrangement shown in FIG. 4b. Actuator A is integrated in the region of plate P which is normally subject to maximum deflection. For this purpose plate P has a corresponding recess in which an actuator A, made with shape memory material or a piezoceramic, is integrated.

The invention claimed is:

1. A method for at least one of influencing mechanical load-bearing capability and loading of an element comprising:
   detecting at least one load correlated characteristic of the element;
   determining a loading state of the element on a basis of the at least one detected characteristic;
   assessing the loading state of the element by determining a dimension which describes a load-bearing capability of the element, where the element would suffer a local or global irreversible damage if the capability is reached or exceeded due to an excessive load application to the element; and
   generating at least one signal on a basis of the assessment of the loading state and on a basis of at least one target function, for at least optimizing a lifetime of the element, wherein at least one signal is sent to at least one actuator, which is integrated within the element or is applied to the element, to activate the at least one actuator for influencing the loading state, so that the element experiences loading or load relief comprising additional stiffening or higher elasticity, in at least one known region exposed to the excessive load application to the element, and wherein the at least one signal for activating the at least one actuator causes a dimension representing the load-bearing capability of the element to be optimized on a basis of the at least one target function.

2. The method according to claim 1, comprising:
   at least one sensor associated with the element, for detecting the at least one loading characteristic.

3. The method according to claim 2, wherein:
   the at least one loading characteristic varies under at least one of static and dynamic loading of the element.

4. The method according to claim 1, comprising:
   at least one sensor for detecting a mechanical thermal characteristic of the element which varies in a load conditioned structural deformation.

5. The method according to claim 1, wherein:
   the load-bearing capability of the element is determined by accessing a database in which are stored known loading states of the element which can be assigned to the at least one loading characteristic.

6. The method according to claim 1, wherein:
   the at least one loading characteristic and the influencing of the loading state by the actuator are detected with a converter material.

7. The method according to claim 1, wherein:
   a force or an expansion value, derived from a load-conditioned deformation of the element, comprises the at least characteristic.

8. A device for influencing mechanical load-bearing capability of an element comprising:
   at least one sensor associated with the element, each sensor generating a load correlated sensor signal;
   an evaluation unit for evaluating each loading correlated sensor signal and assigning a characteristic to each loading correlated sensor signal;
   a storage for storing previously known loading states of the element from which the evaluation unit selects and evaluates a loading state as a function of the characteristic;
   at least one actuator; and
   an actuator unit, coupled to the storage, for activating the at least actuator in response to each loading correlated sensor signal, which is integrated into the element or is applied to the element, so that the element is loaded or load relieved in at least in one local region as a function of the evaluated loading state so that a load-bearing capability of the element is optimized on a basis of at least one target function for at least optimizing a lifetime of the element.

9. The device according to claim 8, wherein:
the at least one sensor generates the load-correlated sensor signal dependent on an element deformation caused by the at least one of a static and a dynamic load.

10. The device according to claim 8, wherein:
at least one of the at least one sensor and the at least one activator comprises a converter material.

11. The device according to claim 10, wherein
the converter material comprises at least one of:
a piezoceramic, a lead-free piezoceramic, a piezopolymer, an electrostrictive ceramic, an electrorheological fluid, a polymer gel, a magnetorheological fluid, a shape memory alloy, and a shape memory polymer.

12. The device according to claim 8, wherein:
the evaluation unit, the storage and the at least one actuator unit are integrated into the element or applied to the element.

13. The device according to claim 8, wherein:
an energy source is integrated into the element or applied to the element.

14. The device according to claim 8, comprising:
a telemetry unit integrated into the element or applied to the element, which transmits each load correlated sensor signal to the evaluation unit which is separated from the element.

* * * * *